US005108387A

United States Patent [19]

Falk et al.

[11] Patent Number: 5,108,387

[45] Date of Patent: Apr. 28, 1992

[54] COLLAPSIBLE CONTAINER FOR LIQUIDS

[75] Inventors: Guenter Falk, Georgsmarienhuette; Matthias Wesseler, Hilter; Manfred Rycyk, Bissendorf; Bernd Schenk, Waldbronn, all of Fed. Rep. of Germany

[73] Assignee: Cubidor Bernd Schenk KG, Bretten, Fed. Rep. of Germany

[21] Appl. No.: 478,085

[22] Filed: Feb. 9, 1990

[30] Foreign Application Priority Data

Feb. 11, 1989 [DE] Fed. Rep. of Germany ....... 3904080

[51] Int. Cl.[5] ............ A61M 5/00

[52] U.S. Cl. ............ 604/408; 604/415; 222/475; 215/251

[58] Field of Search ............ 604/408-416; 222/475, 465.1; 215/251

[56] References Cited

U.S. PATENT DOCUMENTS

| | | | |
|---|---|---|---|
| 3,383,017 | 5/1968 | Krings | 222/475 |
| 3,905,368 | 9/1975 | Lewis, Jr. et al. | 604/415 |
| 4,150,673 | 4/1979 | Watt | 604/408 |
| 4,336,802 | 6/1982 | Stone et al. | 604/415 X |
| 4,463,862 | 8/1984 | Hansen | 604/415 X |
| 4,507,114 | 3/1985 | Bohmen et al. | 604/416 X |
| 4,524,809 | 6/1985 | Dent | 604/415 X |
| 4,596,573 | 6/1986 | Donnan et al. | 604/415 |
| 4,834,152 | 5/1989 | Howson et al. | 604/411 X |
| 4,904,235 | 2/1990 | Yaniv et al. | 604/6 |
| 4,923,098 | 5/1990 | Schoonover et al. | 222/465.1 |
| 4,981,464 | 1/1991 | Suzuki | 604/415 |

*Primary Examiner*—Robert A. Hafer
*Assistant Examiner*—Kerry Owens
*Attorney, Agent, or Firm*—Herbert Dubno; Andrew Wilford

[57] ABSTRACT

A collapsible container of a synthetic resin foil for receiving liquid substances, especially dialysis concentrates and having a filling fitting, a discharge fitting and at least one grip in which one or both of the fittings can be integrated.

9 Claims, 2 Drawing Sheets

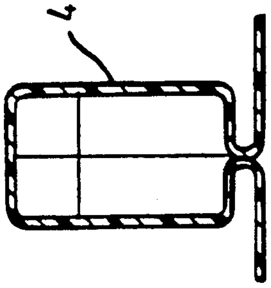
FIG.4
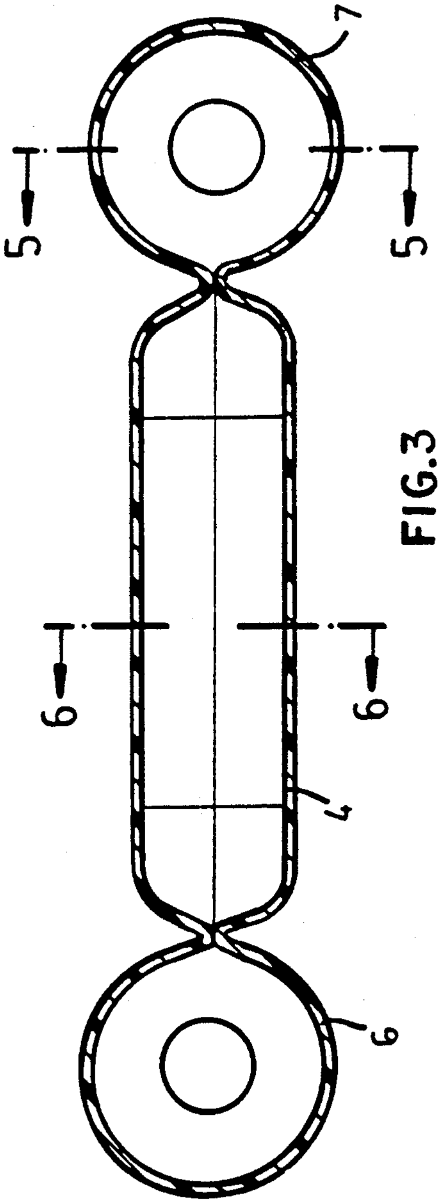
FIG.3
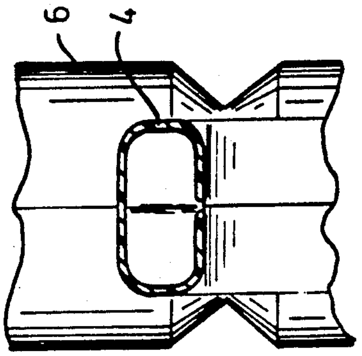
FIG.6
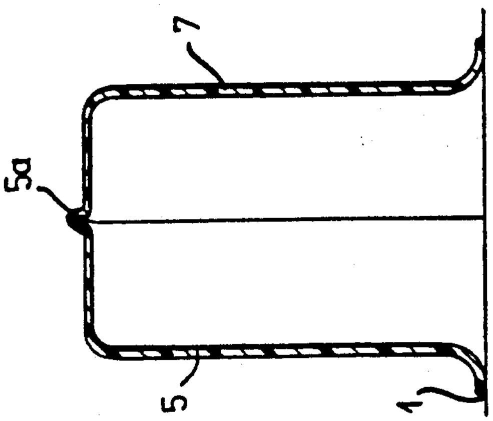
FIG.5
FIG.7
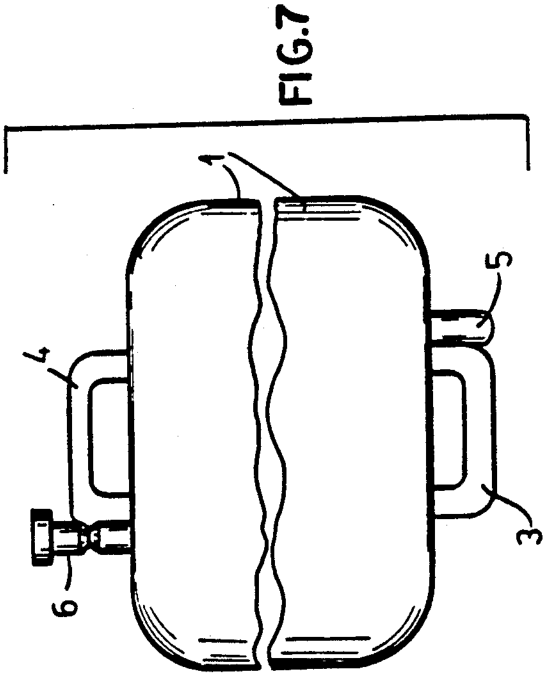

COLLAPSIBLE CONTAINER FOR LIQUIDS

FIELD OF THE INVENTION

Our present invention relates to a collapsible container, composed of a plastic foil, serving as a receptacle for liquids, especially dialysis concentrates. More particularly, the invention relates to a collapsible receptacle, especially for the purposes described and having a filling fitting for introduction of the liquid into the receptacle, a discharge fitting for the discharge of the contents of the receptacle from the latter, and at least one grip or handle which facilitates manipulation of the receptacle.

BACKGROUND OF THE INVENTION

Receptacles of the type are known and are used for a wide variety of purposes and in many applications. By and large, these applications are limited as to daily use and/or in technological applications of the receptacle. Specifically, the state of the art receptacles of this type have not been found to be applicable for all purposes and all fields because of certain inherent drawbacks in prior art designs.

For reasons which are not fully understood and may be a result of latent prejudice against the use of such receptacles for pharmaceutical substances like dialysis concentrates, such receptacles have not been widely employed for the transport, preservation and preparation of dialysis concentrates for dialysis machines as well as in respect of disposal of the dialysis concentrate receptacles after use.

For the transport and preservation of dialysis concentrates, even today and in most cases, rigid large-volume canisters are provided for the dialysis concentrate which is accessible through a screwcap mouth. When the canister is placed in use, the screwcap must be removed and the extraction lance of the dialysis machine must be inserted in the canister and immersed in the dialysis concentrate through the mouth which is opened by the removal of the screwcap. This manipulation technique is associated with a number of problems.

Firstly, the disposal of the relatively large rigid canisters is a problem. In medical practice and where a multiplicity of dialysis stations are in operation in parallel, it is not uncommon for the empty dialysis canisters to be stored before ultimate disposal and ultimately disposed of because the problem of sterilization limits the possibility of reuse of the canisters. Since the volume occupied by the canisters is substantial, this requires considerable spacing for holding the used canisters until disposal and actually makes the disposal problem severe. Space is generally not readily available in medical facilities.

The canisters, in addition, must be opened before filling and use to allow, in the latter case, the extraction lance to be inserted. Since the interior of the canister is fully accessible upon such opening, there is a significant danger than contaminants will be entrained to the dialysis concentrate and hence of secondary contamination.

With respect to the problem of disposal, it has been recognized that the large volume of canisters creates significant disposal problems and hence it has been suggested to provide foil bags which are collapsible and are made up of one or more foil layers. In the past, these foil bags have been found to be suitable only for relatively low volumes because the weld seams weren't able to sustain stresses resulting from sudden shocks, like a fall of the filled bag. As a consequence, there was always a danger of leakage.

Furthermore, because of the shape instability of the highly flexible foil bags they could not readily be placed upon a dialysis machine and, as a result, it was necessary to provide special suspending means on the bag and complementary suspending means on the dialysis machine or on a separate infusion stand. In the latter case the radius of movement of the dialysis machine on its casters was greatly limited.

OBJECTS OF THE INVENTION

It is the principal object of the present invention to provide an improved container or receptacle for liquids, especially dialysis concentrates, whereby the aforedescribed drawbacks are obviated.

Another object of this invention is to facilitate the handling of liquid substances, especially dialysis concentrates, by providing a container or receptacle which is easy to handle, sterile, simple to bring into position and readily disposed of.

SUMMARY OF THE INVENTION

These objects and others which will become apparent hereinafter are attained, in accordance with the invention with a container for dialysis concentrate liquids which comprises a handle formed at least along one side of the container and a fitting formed unitarily with and constituting part of the handle, the fitting being a filling fitting or a discharge fitting. Both the filling fitting and the discharge fitting can be integrated with the handle and the collapsible receptacle can be formed with two handles on opposite sides, one of which has both fittings or wherein each of the handles has a respective one of the fittings.

According to the invention, therefore, the handle or grip is integrated with the filling fitting and/or the discharge fitting. According to the invention, the collapsible receptacle which can be composed of a foil is constructed to collapse upon emptying of the dialysis concentrate with the discharge thereof without varying the length and breadth of a resting surface with which the receptacle is supported on the dialysis machine or some other supporting surface. This permits the receptacle, by appropriate choice of its resting surface to be placed upon the usual support device in the dialysis machine and to fall inwardly above this resting surface. The material thickness of the plastic used is thus so selected that the receptacle will maintain its seal even when subjected to a strong mechanical load, e.g. a shock or fall. The synthetic resin or plastic material is preferably a material of good deformability, strength and ease of disposal, especially LDPE (low-density polyethylene) or LLDPE (linear low-density polyethylene).

According to a feature of the invention, the filling fitting and the discharge fitting are both provided on one and the same grip, preferably at opposite ends thereof directly.

When two such grips are provided at opposite sides of the receptacle, one of them can be formed with the filling fitting while the other is formed with the discharge fitting.

According to a further feature of the invention, the discharge fitting is provided with a plug of elastomeric material which, to facilitate insertion of the liquid extraction lance may be partially weakened by a slit which can be formed therein.

The discharge fitting may have a coded tube or outlet formation ensuring that it can only be connected to the appropriate extraction lance of the dialysis machine.

According to another feature of the invention, the discharge fitting is closed by a closure cover or cap which has an annular groove form-fittingly receiving and sealed to the free end of the discharge fitting which can be formed from the synthetic resin or plastic material of the receptacle. In this groove, a metal ring can be received so that, with inductive heating of the ring, the end of the discharge fitting can be fused or welded closed to the cap to set the two together.

The two-grip construction greatly facilitates handling and transportation of the container which can hold very large volumes. The discharging fitting can also be provided with a sealing membrane, which signals, while it remains intact, that the contents have not been contaminated.

BRIEF DESCRIPTION OF THE DRAWING

The above and other objects, features and advantages of our invention will become more readily apparent from the following description, reference being made to the accompanying highly diagrammatic drawing in which.

Figure 1:
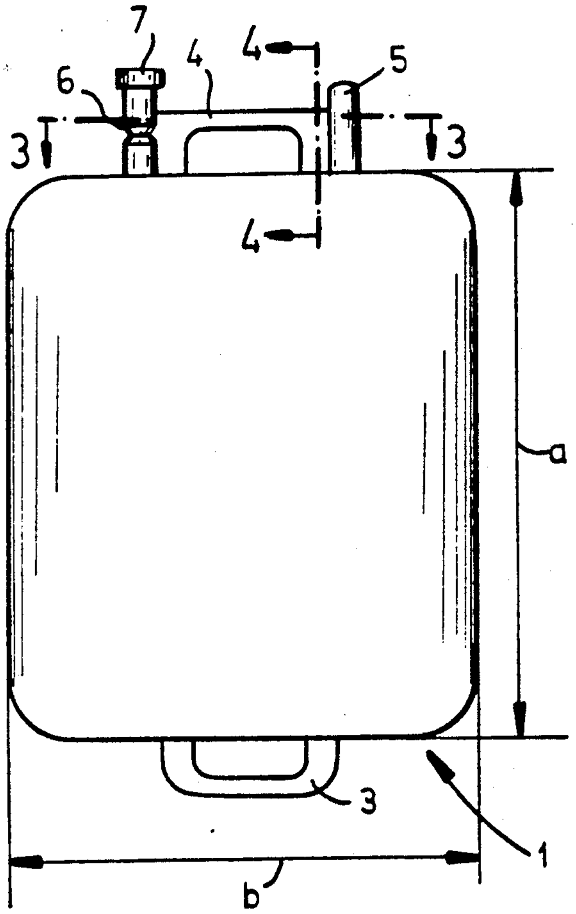
FIG. 1 is an elevational view of a container of the present invention having two grips.
Figure 2:
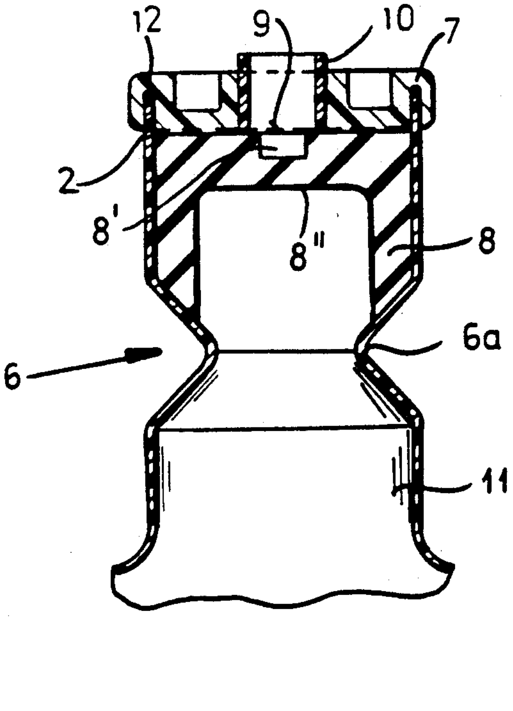

FIG. IA is a side view of the container of FIG. 1;

FIG. 2 is a cross sectional view through a detail of the discharge fitting of FIGS. 1 and IA;

FIG. 3 is a cross sectional view through the handle of FIG. 1 taken along the line 3—3 of FIG. 1;

FIG. 4 is a sectional view taken along the line 4—4 of FIG. 1;

FIG. 5 is a sectional view taken along the line 5—5 of FIG. 3; FIG. 6 is a sectional view taken along the line 6—6 of FIG. 3; and FIG. 7 is a view of an embodiment of the invention in which each of the two grips has a respective one of the fittings.

SPECIFIC DESCRIPTION

Figure 1A:
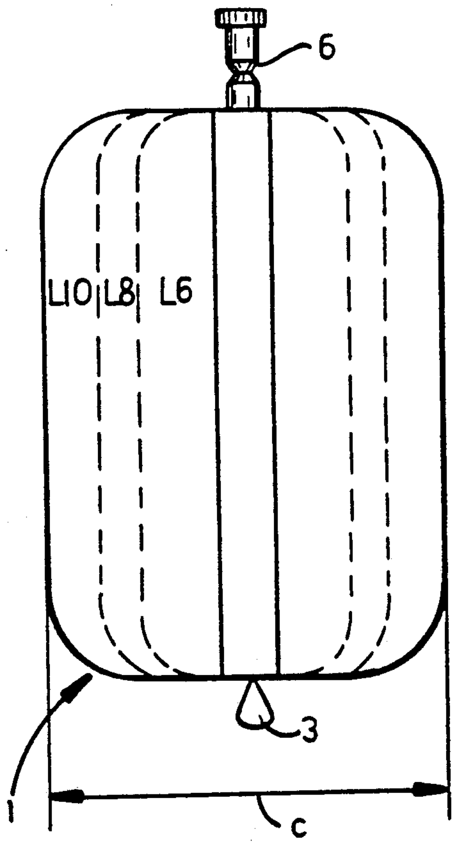

FIGS. 1 and 1A show a generally cubical receptacle 1 whose corners and edges are rounded and which has a length a and a width b determining base surfaces which can serve as resting surfaces (FIG. 1) of constant area. These surfaces remain constant even as the contents of the vessel are removed and the remainder of the vessel collapses onto the resting surface. As can be seen from the side view of FIG. 1A, the height c of the container can vary depending upon the different volumes container therein which may be 6, 8 or 10 liters, corresponding to the heights c shown at L6, L8 and L10 respectively. The container can be placed upon a support surface of the dialysis machine and emptied in the manner described. The container may also be suspended from one of its handles. At the opposite ends, the container 1 is formed unitarily with respective grips 3 or 4 facilitating transport and mounting of the container, e.g. by suspension from an infusion stand. This, of course can be accomplished with a single grip although for handling large volume containers of this type, the two grips are preferred. The grips are located centrally at the end faces of the container.

In a preferred embodiment of the invention, one of the grips, e.g. the grip 4 in FIGS. 1 and 1A, is so constructed that a filling fitting 5 and a discharge fitting 6 for the liquid are integrated therewith. The grips, filling fitting and discharge fitting are formed of the material from the container during the formation thereof. The filling fitting at least is permanently closed following filling as represented by the heat seal 5*a* shown for the filling fitting 5 in FIG. 5. Both the filling fitting and the discharge fitting can be similarly closed or enclosed during formation and the container can be sterilized and delivered to the filling station in the pharmaceutical plant in this fashion.

For filling, the end of the fitting 5 is cut off and after filling is welded closed again to ensure a hermetic seam and a minimum retention of the contents of the receptacle upon emptying and collapse of the receptacle.

The emptying fitting 6 may originally be closed and can be provided in the filling station with a plug 8 and a cap 7 which hermetically seals in a sterile manner the container while allowing the insertion of an extraction lance to discharge the contents of the container. From a point of view of the material used the cap 7 is selected to be compatible with the material of the container and thereby ensure an effective seal between them.

The outlet fitting 6 has been shown in cross section in FIG. 2. It has an annular constriction 6*a* below the free end of this fitting and receives a plug 8 of an elastomeric material, e.g. rubber. The plug 8 rests against the constriction and is set below the free end of the outlet fitting. On the collar of the outlet fitting 6 which projects above the plug 8, the cap 7 is mounted.

The cap 7 has a circumferential annular groove 2 which, prior to receiving the end of the fitting 6, has been provided with a metal ring 12, preferably a ring of stainless steal.

By inductive heating of this metal ring, the cap 7 and the free end of the fitting 6 engaged in the groove 2 can be welded together. The cap 7, therefore, closes the outlet fitting 6.

Between the cap 7 and the plug 6 is a safety seal or sealing membrane 9 which is clamped between the plug and the cap 7 relative to the discharge fitting 6. If dialysis concentrate is to be extracted from the interior of the container, the extraction lance is forced through the membrane 9 and the plug 8 to immerse in the dialysis liquid while the plug seals the lance against contamination of the content of the container.

In a preferred embodiment of the invention, the plug 8 has a weakened portion 8″ which can have a slit 8′ stamped therein to facilitate penetration by the lance and corresponding stressing of the rubber plug around the lance to maintain the seal. The thin portion 8″ and the recess 8′ can also be provided at the lower end of the plug. With this arrangement, as is known with respect to dispensing vials of hypodermic syringes, upon removal of the lance, the interior of the container 1 will be resealed.

The discharge fitting 6 and preferably its cap, can have a coded tubular fitting or formation 10 shaped with respect to the contents of the container so that it will only cooperate with the content-specific cross section of the extraction lance so that, for example, acetate or bicarbonate solutions will not inadvertently be delivered to the wrong location. This, of course, ensures that the correct dialysis concentrate will be provided to appropriate extraction lances of the machine and avoid contamination of the latter.

As can be seen from FIG. 7, the container 1 can have its grips 3 and 4 formed with the inlet fitting 5 and the outlet fitting 6 respectively by the pinched seams 20, 21, 22. Of course it is also possible to integrate the filling fitting with the grip and to provide the discharge fitting elsewhere on the container, e.g. laterally thereof. The discharge fitting can be integrated with a grip while the filling fitting is provided elsewhere on the container. Naturally, in accordance with the principles of the invention only a single grip ca be provided.

With respect to the configuration of the outlet fitting 6, it should be noted that with the aforementioned annular constriction 6*a* and the transition to the interior of the container 1, a free space 11 (FIG. 2) is provided into which the lance penetrates without extending therebeyond Upon collapse of the container, therefore, a wall of the container will not be permitted to engage the lance point and be damaged thereby so that no contaminants can thereby be introduced.

We claim:

1. A collapsible container composed of a synthetic foil material for receiving a liquid, especially a dialysis concentrate, a filling fitting formed unitarily on said container exclusively from said foil material and delimited by a pinched seam of said foil material for filling said container with liquid, a discharge fitting formed unitarily on said container exclusively from said foil material for discharging liquid from said container and at least one grip formed unitarily on said container exclusively from said foil material to facilitate the handling thereof and at least one of said fittings being formed directly on and integral with said grip while being separated therefrom exclusively by a pinched seam of said synthetic foil material.

2. The container defined in claim 1 wherein both of said fittings are formed on and integrated in said grip.

3. The container defined in claim 1 wherein a further grip is correspondingly formed on said container and each of said fittings is formed on and integrated into a respective one of said grips.

4. The container defined in claim 1 wherein said discharge fitting is provided with an elastomeric plug for closing said discharge fitting.

5. The container defined in claim 4 wherein said plug is partially weakened to facilitate insertion of an extraction lance therethrough.

6. The container defined in claim 5 wherein said plug is partially weakened by the formation of a slit therein.

7. The container defined in claim 1 wherein said container is provided with an outwardly open, contents specific coding tube in said outlet fitting so that only a selected liquid can be stored in and discharged from said container.

8. The container defined in claim 1, further comprising a cap on a free end of said discharge fitting and provided with a circumferential groove receiving said free end and sealed therewith.

9. The container defined in claim 8, further comprising a metal ring in said groove heatable by inductive heating to weld said free end to the material of said cap.

* * * * *